United States Patent
Nebe et al.

[11] Patent Number: 5,347,358
[45] Date of Patent: Sep. 13, 1994

[54] REFRACTOMETER

[75] Inventors: Wolfgang Nebe; Rolf Godat, both of Jena, Fed. Rep. of Germany

[73] Assignee: Carl Zeiss Jena GmbH, Jena, Fed. Rep. of Germany

[21] Appl. No.: 94,524

[22] Filed: Jul. 20, 1993

[30] Foreign Application Priority Data

Jul. 20, 1992 [DE] Fed. Rep. of Germany ....... 4223840

[51] Int. Cl.$^5$ .................... G01N 21/03; G01N 21/41
[52] U.S. Cl. .................. 356/128; 356/130; 356/132; 356/246
[58] Field of Search ............. 356/128, 130, 131, 132, 356/134, 135, 137, 246

[56] References Cited
FOREIGN PATENT DOCUMENTS 254069 2/1988 Fed. Rep. of Germany.
4038123 6/1991 Fed. Rep. of Germany.
4102376 8/1992 Fed. Rep. of Germany.
1187029 10/1985 U.S.S.R. ................ 356/130

Primary Examiner—F. L. Evans
Attorney, Agent, or Firm—Walter Ottesen

[57] ABSTRACT

The invention relates to a transmitted-light refractometer wherein a slit diaphragm is imaged on a diode array through a cuvette holding the sample. The cuvette itself is arranged in the telecentric beam path. The exit window of the cuvette has several regions in which the inner surfaces of the exit window are inclined differently to the inner surface of the entry window. In this way, several slit images are generated on the diode array and the relative spacings of these images are independent of a possible disadjustment of the condenser and the objective. An embodiment of the invention permits the simultaneous measurement of the refractive index and the absorption of the sample.

12 Claims, 2 Drawing Sheets

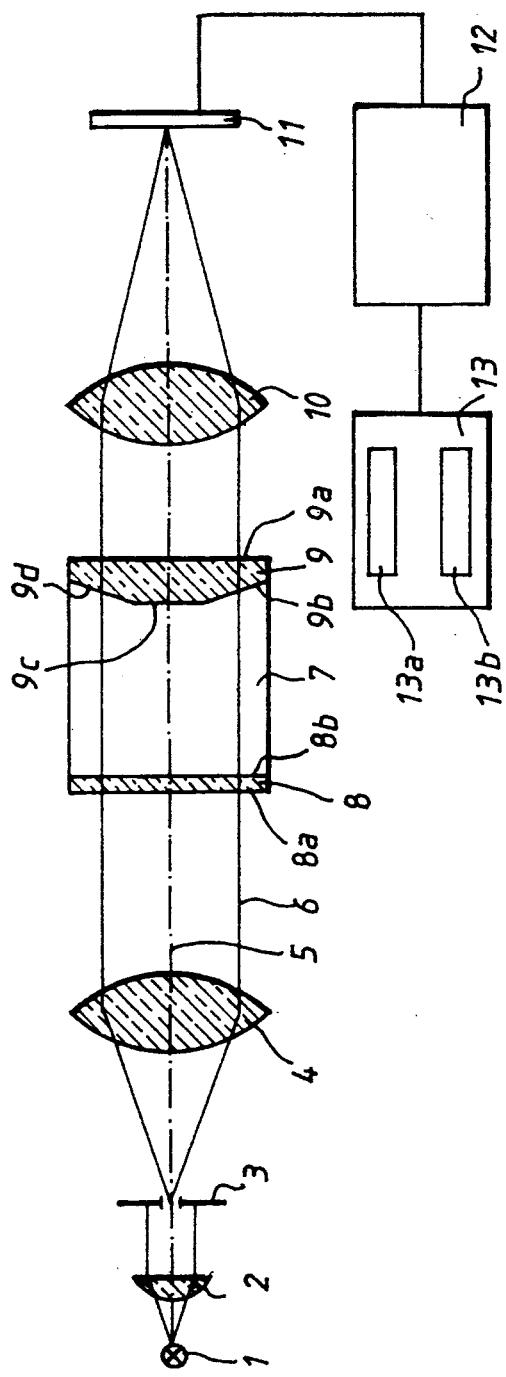
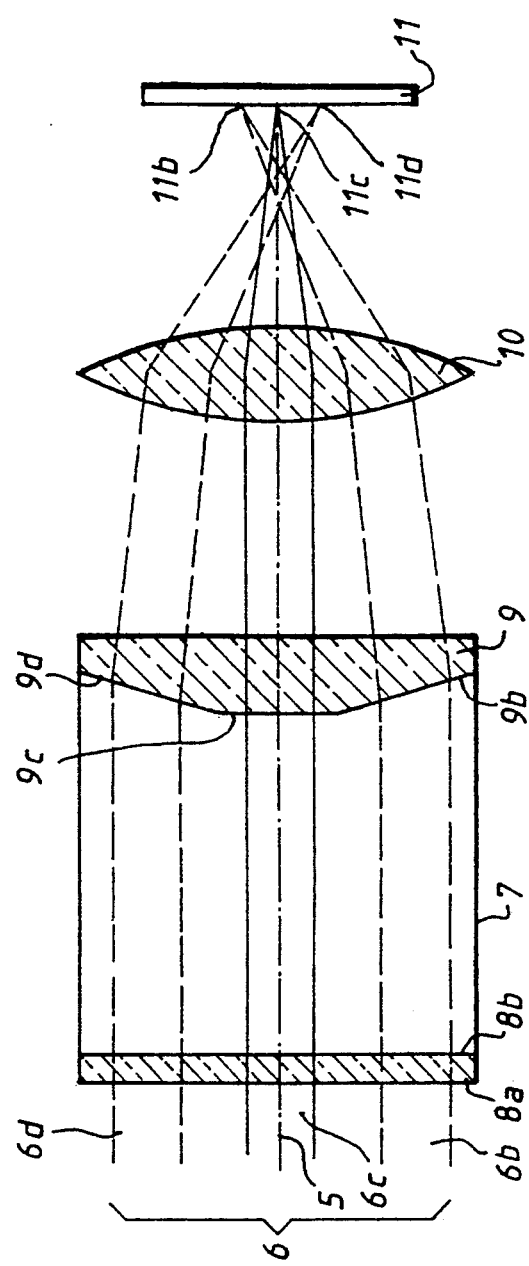

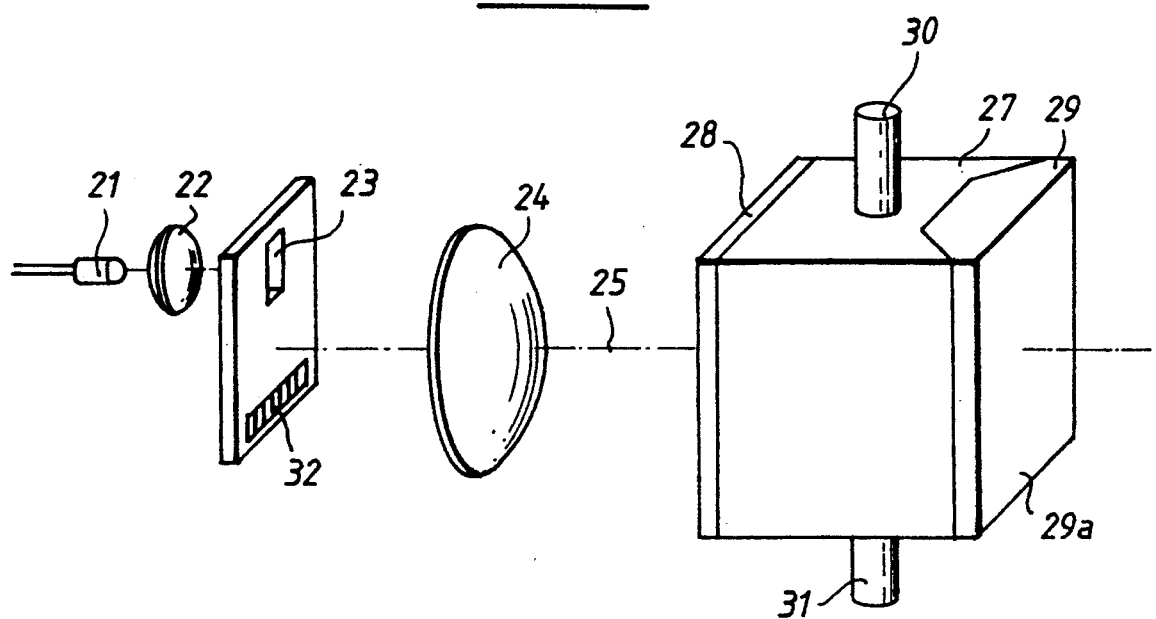
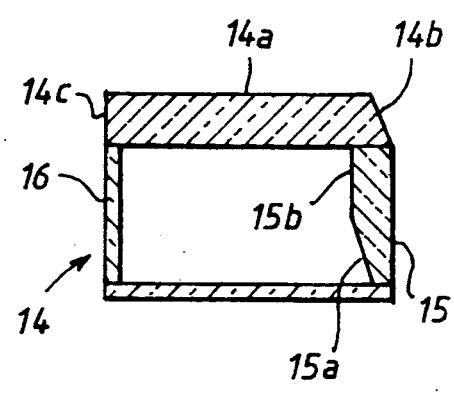
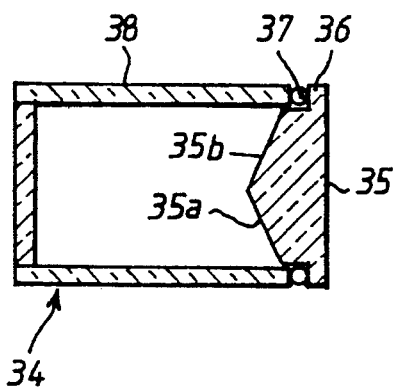

REFRACTOMETER

BACKGROUND OF THE INVENTION

Published German patent application DE-OS 4,102,376 discloses a transmitted-light refractometer which includes a so-called differential cuvette having two prism-shaped chambers. One of the chambers receives the sample liquid and the other chamber receives the reference liquid. The partition between the two chambers is provided by a partition wall inside the cuvette. This partition wall is arranged so as to be inclined to the optical axis.

German patent publication DD 254,069 discloses a transmitted-light refractometer having a cuvette with only a single prismatic chamber. The refractive index measurement is made here without a reference liquid simply with the aid of the beam deflection within the prismatic-shaped sample volume.

The known transmitted-light refractometers all have in common that the refractive index of the sample is determined with the aid of the deflection of the measurement light effected by the prismatic sample volume relative to the deflection registered for a previously conducted calibration measurement with a liquid of known refractive index. A disadjustment of the illumination and viewing optics which occurs in the meantime leads to measurement errors.

Published German patent application DE-OS 4,038,123 discloses a differential refractometer wherein the cuvette is partitioned by a V-shaped wall into a measurement chamber and a reference chamber so that two slit images occur on the line sensor. The volume or cross section available for the through-flow measurement is very small for the sample because of this partition of the cuvette.

Furthermore, so-called total refractometers are known wherein measurement light incidents upon the probe at different angles containing the critical angle of total reflection. The refractive index is determined with the aid of the critical angle of total reflection. One such refractometer is described in European patent publication 0,184,911. Also here, the disadjustments of the optical components occurring after the calibration measurement lead to measurement errors. A further disadvantage is that the measurement result is determined only from an edge layer of the sample which is very thin. This edge layer is, however, generally (for example, for laminar disturbances) not representative of the entire sample. Deposits or small bubbles in the edge layer therefore act to falsify the measurement result.

SUMMARY OF THE INVENTION

It is an object of the invention to provide a transmitted-light refractometer of the kind described above wherein the disadvantages of these known transmitted-light refractometers are avoided while at the same time providing the least possible additional complexity with respect to the apparatus. It is another object of the invention to especially be able to carry out a reference measurement simultaneously with each measurement on the sample.

A refractometer of the invention includes: a light source for generating rays of light; illuminating optic collimating means for collimating the rays to form a collimated light beam defining an optical axis and having a predetermined cross section transverse to the optical axis; a cuvette arranged on the optical axis and defining a hollow enclosed interior space for receiving a sample to be analyzed; the cuvette having a transparent entry window and a transparent exit window for passing the light beam into and out of said interior space, respectively; the entry window having an entry inner surface and the exit window having an exit inner surface and the inner surfaces delimiting the interior space; sensor means disposed downstream of the exit window and defining a plurality of independently registering surface areas for detecting deflections of the light transmitted through the cuvette; the inner surfaces extending over at least two regions of the cross section of the collimated light beam; and, the exit inner surface being subdivided into a plurality of component surfaces arranged in corresponding ones of the regions of the cross section with the component surfaces being inclined at different angles with respect to each other.

According to one of the features of the invention, the windows of the hollow cuvette are in at least two regions over the cross section of the collimated beam and the inner surfaces of the windows are arranged in the two regions at different angles with respect to each other.

The diameter of the collimated beam is then so selected that the two, three or four regions of the hollow cuvette are simultaneously illuminated. The light deflected into the different regions of the hollow cuvette in different directions is focused by a single objective at different positions on the line or surface sensor. A disadjustment of the imaging optics and of the illuminating optics acts simultaneously on the positions of the light points of all regions so that a measured value free of adjustment errors can be determined from the relative spacings of light points on the sensor.

The measurement complexity of the apparatus with respect to the transmitted-light refractometer of published German patent application DE-OS 4,102,376 is simply that the inner side of one of the cuvette windows has several optical surfaces inclined differently with respect to each other. Preferably, the cuvette has a first window with two plane-parallel surfaces and a second window having an outer surface aligned parallel to the surfaces of the first window. The inner surface of the second window at one component surface thereof can likewise be parallel to the inner surface of the first window. The light passing through this component surface then supplies the zero position on the sensor.

A maximum volume for receiving the sample or a maximum cross section for passing the sample when conducting flow measurements is provided with the smallest possible cuvette dimensions because the different regions are realized with respect to the configuration of the inner surfaces of the entry and exit windows.

In a preferred embodiment of the invention, the inner surface of the second window has two component surfaces in which this inner surface is inclined to the inner surface of the first window at angles of the same value but mutually opposed to each other. The spacing of the light points on the sensor is then independent of a possible disadjustment of the optics. Furthermore, the advantage is provided that the measurement sensitivity is doubled because of the deflection of the light in mutually opposite directions effected by the double prism.

In the refractometer according to the invention, the index of refraction of the sample is determined from the geometric position of the light points on the sensor. For this reason, the transmission of the sample can be determined by means of an additional evaluation of the transmitted light intensity. An additional light path uninfluenced by the sample (for example, in the side wall of the cuvette) can be provided for obtaining a reference value required for this purpose.

After an appropriate evaluation of the sensor signals, the refractive index and absorption of the sample can be shown on a display device simultaneously and without too much additional opto-mechanical complexity.

The refractometer can be a single-pass arrangement wherein the cuvette transmits the measurement light only once. The sensor is then arranged in the focal plane of an objective interposed between the cuvette and the sensor.

A doubled measuring accuracy accompanied with only a slight complexity, however, results when the sensor is mounted in the illuminating-side focal plane of the illuminating optics and a reflecting surface is provided on the side of the cuvette facing away from the illuminating optics. For this purpose, the outer surface of the second cuvette window can be mirrored.

To adjust different measuring regions, the second cuvette window or the entire cuvette can be exchanged for one wherein the angle of inclination of the component surfaces to the optical axis is different. Furthermore, the cuvette can be configured as a through-flow cuvette.

BRIEF DESCRIPTION OF THE DRAWINGS

The invention will now be described with reference to the drawings wherein:

FIG. 1 is a schematic representation of the beam path in a refractometer according to a first embodiment of the invention;

FIG. 2 is an enlarged representation of the region of the embodiment of FIG. 1 at the sensor end;

FIG. 3 is a perspective schematic of a refractometer according to a second embodiment of the invention with a through flow cuvette;

FIG. 4a is a schematic of a cuvette shown in section for the simultaneous measurement of refractive index and absorption; and, FIG. 4b is a schematic of an additional cuvette shown in section having an exchangeable exit window.

DESCRIPTION OF THE PREFERRED EMBODIMENTS OF THE INVENTION

The refractometer shown in FIG. 1 includes a monochromatic light source in the form of a laser diode 1. The light of the light source uniformly illuminates a slit diaphragm 3 through a collector 2. The slit diaphragm 3 is arranged in the focal plane of the condenser 4 which images the slit diaphragm 3 at infinity.

The hollow cuvette 7 is arranged in the telecentric beam path 6 behind the condenser 4. The hollow cuvette 7 has an illuminating-end entry window 8 in the form of a plane-parallel glass plate having plane-parallel surfaces (8a, 8b) aligned to be perpendicular to the optical axis 5 of the condenser 4. The cuvette 7 has a second glass window 9 which serves to allow the light to exit. The outer surface 9a of the second window 9 as well as the center region 9c of the inner surface are likewise aligned perpendicular to the optical axis 5. The exit window 9 has two peripheral regions (9b, 9d) in which the respective inner surfaces are oppositely inclined at the same angle to the optical axis 5.

The sample liquid to be analyzed is enclosed between the inner surface 8b of the entry window 8 and the exit window 9. Different prism-shaped component volumes occur in the interior of the cuvette because of the different inclinations of the inner surfaces of the exit window in the regions (9b, 9c, 9d). The light is deflected in different directions in these component volumes as will be explained in detail with respect to FIG. 2.

A line-shaped sensor 11 (a diode array) is arranged behind the cuvette 7 in the focal plane of the objective 10. A total of three images of the slit diaphragm 3 occur on the sensor 11 because of the different prism shapes of the components volumes. The refractive index of the sample is computed from the positions of the slit images in an evaluation device 12 connected downstream and the result is shown on a display 13b.

The display unit 13 has a second display 13a which is provided to show the probe absorption. The second display is used when the cuvette 7 is exchanged for the cuvette of FIG. 4a.

For the purpose of providing a more detailed explanation, the differently-inclined inner component surfaces (9b, 9c, 9d) of the exit window 9 are assigned to respective component beams of the collimated light beam 6 identified by reference numerals (6b, 6c, 6d). The center component beam 6c passes through the center region 9c parallel to the surfaces (8a, 8b) of the entry window and generates a slit image 11c on the optical axis 5 via the objective 10. The two outer component beams (6b, 6d) are deflected in mutually-opposite directions at the same angle at the component surfaces (9b, 9d) of the exit window. The objective generates two further slit images (11b, 11d) on the sensor 11 from these deflected component beams.

The positions of the slit images (11b, 11c, 11d) change in the same manner with a change of alignment of the objective 10 relative to the condenser (not shown in FIG. 2). The spacings of the slit images (11b, 11c, 11d) to each other, however, remain constant. The evaluation of these spacings which follow is therefore not burdened with such disadjustment errors.

The slit image 11c remains in its position when the cuvette 7 is rotated about an axis perpendicular to the plane of the drawing; whereas, the spacings of the slit images (11b, 11d) to the slit image 11c change differently. The computed refractive index is free of errors by considering these different spacing changes. These errors are caused by a defective alignment of the cuvette 7 to the optical axis 5.

The embodiment shown in FIG. 3 operates in autocollimation. The through-flow cuvette 27 has an inlet line 30 and an outlet line 31 and corresponds essentially to the cuvettes described previously. However, here the surface 29a of the second window 29 is mirrored and is parallel to the two surfaces of the entry window 28. A slit diaphragm 23 and a diode array 32 are arranged on a common carrier one above the other in the illuminating-end focal plane of the condenser 24. The slit diaphragm 32 is uniformly illuminated by light source 21 and collector 22.

The condenser 24, in turn, images the slit 23 at infinity. After reflection at the outer surface 29a of the second cuvette window, the collimated light beam passes through the sample a second time in the opposite direction. The condenser 24 simultaneously acts here as an imaging objective and generates three slit images on the diode array 32 with the images being spaced from each other. The evaluation itself takes place in the same manner as described with respect to the embodiment previously described; however, the light deflection is doubled because of the two-time passthrough.

A cuvette 34 having an exchangeable exit window 35 is shown in FIG. 4b. The exit window 35 has a widened edge region 36 with which it is attached to the end faces of the side walls 38 of the cuvette 34. A sealing ring 37 is provided between the edge region 36 and the side walls 38.

The exit window 35 is exchangeable for a second exit window in dependence upon the measuring task. In the second exit window, the inner surfaces (35a, 35b) can, for example, be inclined to each other at another angle whereby another measuring region and another measuring resolution can be adjusted. Exit windows can especially be provided wherein the inclined inner surfaces are configured similar to an echelette grating. However, the groove spacing can be selected to be substantially greater than the light wavelength and be up to several millimeters. The optical path length in the sample, and therefore the absorption, is then approximately constant across the entire cross section of the cuvette.

The cuvette 14 in FIG. 4a has an exit window 15 with an inner surface 15b parallel to the surfaces of the entry window 16. The exit window 15 also has an inner surface 15a inclined with respect to inner surface 15b. A side wall 14a of the cuvette 14 is configured so as to be thicker. A component beam reaches the line sensor through the side wall 14a uninfluenced by the sample liquid. The intensity of the corresponding slit image acts as a reference for the absorption measurement. The absorption itself is determined with the aid of the intensity of the light transmitted through the region 15b. At the same time, the position of the slit image serves as a reference for the refractive-index measurement. The end faces (14b, 14c) of the side wall are inclined to each other to provide a spatial separation of the individual slit images. The side wall serves as a reference beam path.

A temperature measurement should be made on the cuvette since the refractive index of a liquid is greatly dependent on temperature. The temperature of the sample can then likewise be shown on the display unit 13. It is, however, also possible to hold the temperature of the cuvette constant by means of a control loop known per se.

It is understood that the foregoing description is that of the preferred embodiments of the invention and that various changes and modifications may be made thereto without departing from the spirit and scope of the invention as defined in the appended claims.

What is claimed is:

1. A refractometer comprising:
a light source for generating rays of light;
illuminating optic collimating means for collimating said rays to form a collimated light beam defining an optical axis and having a predetermined cross section transverse to said axis;
a cuvette arranged on said axis and defining a hollow enclosed interior space for receiving a sample to be analyzed;
said cuvette having a transparent entry window and a transparent exit window for passing said light beam into and out of said interior space, respectively;
said entry window having an entry inner surface and said exit window having an exit inner surface and said inner surfaces delimiting said interior space;
sensor means disposed downstream of said exit window and defining a plurality of independently registering surface areas for detecting deflections of the light transmitted through said cuvette;
said inner surfaces extending over at least two regions of said cross section of said collimated light beam; and,
said exit inner surface being subdivided into a plurality of component surfaces arranged in corresponding ones of said regions of said cross section with said component surfaces being inclined at different angles with respect to each other.

2. The refractometer of claim 1, said sensor means being a line sensor.

3. The refractometer of claim 1, said sensor means being a surface sensor.

4. The refractometer of claim 1, one of said component surfaces and said entry inner surface being mutually parallel in one of said regions of said cross section.

5. The refractometer of claim 1, two of said component surfaces being in corresponding ones of said two regions and being arranged at the mutually opposite equal angles with respect to each other.

6. The refractometer of claim 5, said two regions of said cross section being first and second regions and said cross section having a third region; said two component surfaces of said exit inner surface being first and second component surfaces and said exit inner surface having a third component surface in said third region and said third component surface being parallel to said entry inner surface.

7. The refractometer of claim 1, said cuvette including means for defining a beam path uninfluenced by the sample.

8. The refractometer of claim 1, further comprising an objective arranged on said axis and being interposed between said cuvette and said sensor means; said objective defining a focal plane; and, said sensor means being mounted in said focal plane.

9. The refractometer of claim 1, said collimating means defining a focal plane between said light source and said collimating means; said sensor means being disposed in said focal plane; said exit window having an outer surface facing away from said collimating means; and, said cuvette having reflective means formed on said outer surface of said exit window.

10. The refractometer of claim 1, one of said windows being exchangeable.

11. The refractometer of claim 1, further comprising an evaluation and display device connected to said sensor means for providing a simultaneous display of the refractive index and absorption of said sample.

12. The refractometer of claim 1, said cuvette being a through-flow cuvette.

* * * * *

UNITED STATES PATENT AND TRADEMARK OFFICE
CERTIFICATE OF CORRECTION

PATENT NO. : 5,347,358
DATED : September 13, 1994
INVENTOR(S) : Wolfgang Nebe and Rolf Godat It is certified that error appears in the above-identified patent and that said Letters Patent is hereby corrected as shown below:

In column 3, line 39: delete "through flow" and substitute -- through-flow -- therefor.

In column 4, line 11: delete "components" and substitute -- component -- therefor.

In column 4, line 64: delete "all" and substitute -- an -- therefor.

Signed and Sealed this

Fifteenth Day of November, 1994

Attest:

BRUCE LEHMAN

*Attesting Officer*  *Commissioner of Patents and Trademarks*